United States Patent
Kerr et al.

(10) Patent No.: US 8,436,156 B2
(45) Date of Patent: May 7, 2013

(54) METHOD FOR THE PRODUCTION OF SUCRALOSE

(75) Inventors: John Kerr, South Croydon (GB); Robert Jansen, Portella LRS (PT); Duane A. Leinhos, Satsuma, AL (US); James Edwin Wiley, Jr., Daphne, AL (US); Sebastien Camborieux, Walton-on-Thames (GB); Anthony Baiada, Dagenham (GB); Gordon Walker, Goring Heath (GB); Carlo Maffezzoni, Via C. Battisti (IT)

(73) Assignee: Tate & Lyle Technology Limited, London (GB)

( * ) Notice: Subject to any disclaimer, the term of this patent is extended or adjusted under 35 U.S.C. 154(b) by 831 days.

(21) Appl. No.: 12/345,998

(22) Filed: Dec. 30, 2008

(65) Prior Publication Data

US 2009/0264633 A1    Oct. 22, 2009

Related U.S. Application Data

(60) Provisional application No. 61/010,180, filed on Jan. 4, 2008.

(51) Int. Cl.
C07H 15/00 (2006.01)
(52) U.S. Cl.
USPC .................................................. 536/18.5
(58) Field of Classification Search ............... 514/18.5; 536/18.5
See application file for complete search history.

(56) References Cited

U.S. PATENT DOCUMENTS

| | | | |
|---|---|---|---|
| 4,362,869 A | 12/1982 | Jenner et al. | |
| 4,380,476 A | 4/1983 | Mufti et al. | |
| 4,405,654 A | 9/1983 | Lee | |
| 4,783,526 A | 11/1988 | O'Brien et al. | |
| 4,826,962 A | 5/1989 | Rathbone et al. | |
| 4,889,928 A | 12/1989 | Simpson | |
| 4,950,746 A | 8/1990 | Navia | |
| 4,980,463 A * | 12/1990 | Walkup et al. ............ 536/124 | |
| 5,023,329 A | 6/1991 | Neiditch | |
| 5,034,551 A | 7/1991 | Vernon et al. | |
| 5,089,608 A | 2/1992 | Walkup et al. | |
| 5,128,248 A | 7/1992 | Dordick et al. | |
| 5,141,860 A | 8/1992 | Bornemann et al. | |
| 5,270,071 A | 12/1993 | Sharp et al. | |
| 5,272,137 A | 12/1993 | Blase et al. | |
| 5,298,611 A | 3/1994 | Navia et al. | |
| 5,354,902 A | 10/1994 | Merciadez et al. | |
| 5,374,659 A | 12/1994 | Gowan | |
| 5,384,311 A | 1/1995 | Antenucci et al. | |
| 5,397,588 A | 3/1995 | Antenucci et al. | |
| 5,409,907 A | 4/1995 | Blase et al. | |
| 5,426,220 A | 6/1995 | Baniel et al. | |
| 5,440,026 A | 8/1995 | Kahn et al. | |
| 5,470,969 A | 11/1995 | Sankey et al. | |
| 5,498,709 A | 3/1996 | Navia et al. | |
| 5,530,106 A | 6/1996 | Navia et al. | |
| 5,593,696 A | 1/1997 | McNally et al. | |
| 5,621,005 A | 4/1997 | Gowan | |
| 5,658,919 A | 8/1997 | Ratnaraj et al. | |
| 5,674,522 A | 10/1997 | Shah et al. | |
| 5,817,340 A | 10/1998 | Roche et al. | |
| 5,876,759 A | 3/1999 | Gowan | |
| 5,977,349 A * | 11/1999 | Catani et al. ............ 536/124 | |
| 6,080,481 A | 6/2000 | Ochs et al. | |
| 6,090,401 A | 7/2000 | Gowan et al. | |
| 6,176,935 B1 * | 1/2001 | Brahmbhatt ............ 127/52 | |
| 6,211,246 B1 | 4/2001 | Gelotte et al. | |
| 6,258,381 B1 | 7/2001 | Luber et al. | |
| 6,265,012 B1 | 7/2001 | Shamil | |
| 6,277,409 B1 | 8/2001 | Luber et al. | |
| 6,646,121 B2 | 11/2003 | El Kabbani et al. | |
| 6,723,877 B1 * | 4/2004 | Maliszewskyj et al. ...... 564/215 | |
| 6,809,198 B2 | 10/2004 | El Kabbani et al. | |
| 6,890,581 B2 | 5/2005 | Vernon et al. | |
| 6,939,962 B2 | 9/2005 | Clark et al. | |
| 6,943,248 B2 | 9/2005 | Catani et al. | |
| 6,998,144 B2 | 2/2006 | Merkel et al. | |

(Continued)

FOREIGN PATENT DOCUMENTS

DE   102 60 085 A1   7/2004
EP   0043649   1/1982

(Continued)

OTHER PUBLICATIONS

Smith et al, Food Additives Databook, 2003, p. 988.*

(Continued)

*Primary Examiner* — Shaojia Anna Jiang
*Assistant Examiner* — Ganapathy Krishnan
(74) *Attorney, Agent, or Firm* — RatnerPrestia

(57) ABSTRACT

The present invention provides a method for producing sucralose from a feed stream resulting from the chlorination of a sucrose-6-acylate in a reaction vehicle. The feed stream includes a sucralose-6-acylate, the reaction vehicle, water, and salts. The salts include one or more selected from the group consisting of alkali metal chlorides, alkaline earth metal chlorides and ammonium chloride. The method includes:
 (i) deacylation of the sucralose-6-acylate by treatment with a base to afford a product stream comprising sucralose;
 (ii) partial removal of water and, optionally, reaction vehicle from the product stream of (i) in order to cause precipitation of the salts from the product stream;
 (iii) removal of the precipitated salts from the product stream of (ii); and
 (iv) isolation of sucralose from the product stream of (iii).

41 Claims, 1 Drawing Sheet

U.S. PATENT DOCUMENTS

| | | | |
|---|---|---|---|
| 6,998,480 | B2 | 2/2006 | Catani et al. |
| 7,049,435 | B2 | 5/2006 | Catani et al. |
| 2002/0157937 | A1 | 10/2002 | Cockrem et al. |
| 2004/0030124 | A1 | 2/2004 | Catani et al. |
| 2006/0149084 | A1 | 7/2006 | Domschke et al. |
| 2006/0188629 | A1 | 8/2006 | Liesen et al. |
| 2006/0205936 | A1 | 9/2006 | Jia et al. |
| 2006/0276639 | A1 | 12/2006 | Fry |
| 2007/0015916 | A1 | 1/2007 | Kabbani et al. |
| 2007/0100139 | A1 | 5/2007 | Fry |
| 2007/0160732 | A1 | 7/2007 | Deshpande et al. |
| 2007/0227897 | A1 | 10/2007 | Li et al. |
| 2007/0270583 | A1 | 11/2007 | Ratnam et al. |
| 2008/0227971 | A1 | 9/2008 | Leinhos et al. |

FOREIGN PATENT DOCUMENTS

| | | |
|---|---|---|
| EP | 0409549 | 1/1991 |
| EP | 0708110 | 4/1996 |
| EP | 0708110 A2 * | 4/1996 |
| GB | 1 426 018 | 2/1976 |
| WO | WO 00/14052 | 3/2000 |
| WO | WO 02/074403 | 9/2002 |
| WO | WO 03/076453 | 9/2003 |
| WO | WO 03/076454 | 9/2003 |
| WO | WO2005/090374 | 9/2005 |
| WO | WO 2005/090374 A1 * | 9/2005 |
| WO | WO2005/090376 | 9/2005 |
| WO | WO 2006/061855 | 6/2006 |
| WO | WO2006/130169 | 12/2006 |
| WO | WO 2006/130169 A1 * | 12/2006 |
| WO | WO 2007/017899 | 2/2007 |
| WO | WO2007/023505 | 3/2007 |
| WO | WO 2007/023505 A2 * | 3/2007 |
| WO | WO 2007/052304 | 5/2007 |
| WO | WO 2008/004246 | 1/2008 |
| WO | WO 2008/091539 | 7/2008 |

OTHER PUBLICATIONS

Merck Index, 1996, p. 549.*
The Free Dictionary, McGraw-Hill, 2003, pp. 1-2.*
Ault, A.. Techniques and Experiments for Organic Chemistry, 1987, pp. 43-44.*
Grant et al, Chemical Dictionary, 1987, p. 122.*
Chen et al, (Ind. Engg. Chem. Res., 1999, 38, 1605-1610.*
DeSilva, F. Water Quality Products, 2006, 11(4), pp. 1-3.*
Boers, Rutger; UK Search and Examination Report; Application No. GB0803197,3; 7 pp (Jun. 2008).
Schierbaum, et al., Burkhard, "Isolation of Carboxylic Acids from Aqueous Solutions by Extraction with Dialkylcarboxylic Amides/Trialkylamines," Chem. Eng. Technol. 22 (1999) 1, pp. 37-41.
Qin, et al., Yingjie, "Pervaporation Membranes That Are Highly Selective for Acetic Acid Over Water," *Ind. Eng. Chem. Res.*, 42, (2003), pp. 582-595.

* cited by examiner

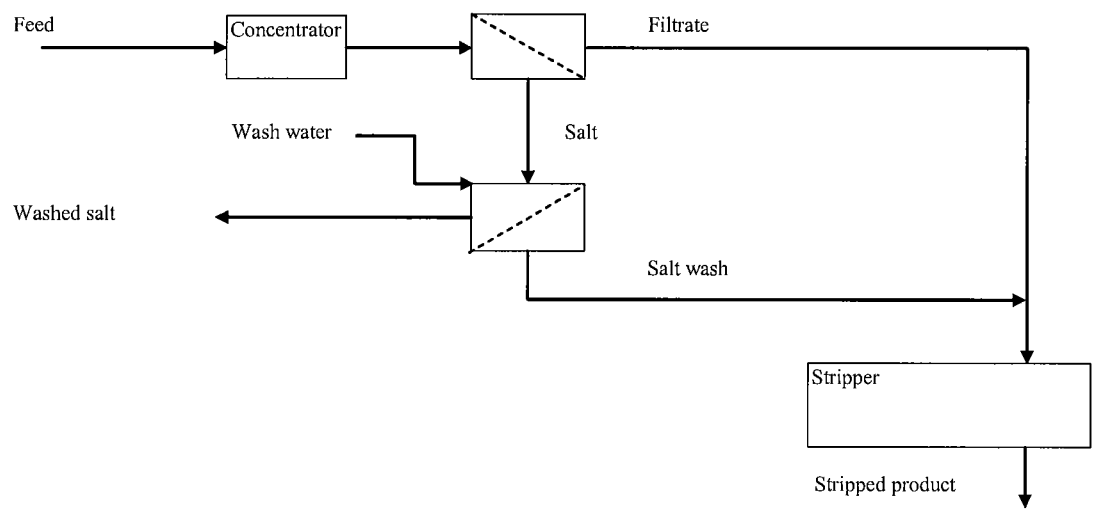

METHOD FOR THE PRODUCTION OF SUCRALOSE

CROSS REFERENCE TO RELATED APPLICATIONS

This application claims priority benefit of U.S. Provisional Application No. 61/010,180, filed Jan. 4, 2008, the entirety of which is incorporated herein by reference.

FIELD OF THE INVENTION

The present invention relates to an improved method for the production of sucralose. In particular, the present invention relates to a method for producing sucralose from a feed stream resulting from the chlorination of a sucrose-6-acylate in a reaction vehicle, said feed stream comprising a sucralose-6-acylate, the reaction vehicle, water, and salts, said salts including one or more selected from the group consisting of alkali metal or alkaline earth metal chlorides and ammonium chloride.

BACKGROUND OF THE INVENTION

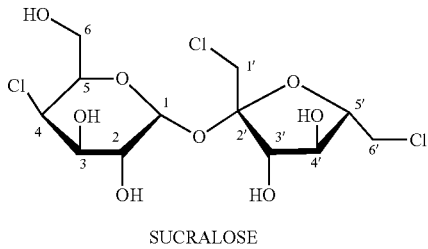

SUCRALOSE

EP 0409549 discloses a process for the chlorination of a sucrose-6-acylate in a tertiary amide reaction vehicle to produce a sucralose-6-acylate, such as sucralose-6-acetate. A large excess of an acid chloride, such as phosgene, is used as the chlorination agent in this process. Following the chlorination reaction, the excess chlorination agent is quenched using a suitable base, thereby forming the chloride salt of the base. The resulting product stream thus comprises a sucralose-6-acylate, the tertiary amide reaction vehicle, water, and salts.

A known method for obtaining sucralose from a product stream comprising a sucralose-6-acylate, a tertiary amide reaction vehicle, water, and salts, without isolation of the sucralose-6-acylate intermediate, is disclosed in EP 0708110. The process comprises deacylation of the sucralose-6-acylate before or after removal of the tertiary amide reaction vehicle, and then isolation of the sucralose. The removal of the tertiary amide (which is usually DMF) is carried out by steam stripping.

According to EP 0708110, it is preferred to perform the deacylation after the removal of the reaction vehicle, because otherwise, during the deacylation step, base-catalysed decomposition of the reaction vehicle, in this case a tertiary amide, occurs. This hinders the subsequent isolation of the sucralose, and also means that the tertiary amide cannot be efficiently recovered and recycled. Thus, the tertiary amide reaction vehicle is removed from an aqueous solution of sucralose-6-acylate, and deacylation of the sucralose-6-acylate is carried out thereafter.

The preferred process according to EP 0708110 requires that a large amount of water is present in the process stream during the removal of the tertiary amide. This is necessary to ensure that the high concentration of salts is maintained in solution, thereby minimising the amount of solids that the process stream has to accommodate. The large amount of water also ensures that the sucralose-6-acylate, which is soluble in the tertiary amide reaction vehicle but less soluble in water, is maintained in solution as the tertiary amide reaction vehicle is removed.

The large amount of water that is present in the process stream of EP 0708110 during the removal of the tertiary amide reaction vehicle has the effect that the removal of the tertiary amide reaction vehicle, for example by steam stripping, is very energy intensive. It would be advantageous if the amount of water present during this operation could be reduced, in order to increase the energy efficiency of the process.

The disadvantages of the known steam stripping process for removal of the reaction vehicle are discussed in WO 2005/090376 and WO 2005/090374. Here it is proposed to remove all liquids from the chlorination feed to provide a solid residue, and to then obtain sucralose from the solid residue. According to this prior art, the removal of the liquids preferably takes place using an agitated thin film dryer.

A further disadvantage associated with the process of EP 0708110 is that the salts are maintained in the process stream and are only removed during the final isolation of sucralose. The presence of high concentrations of salts in the process stream limits opportunities to employ salt-sensitive purification techniques on the process stream. Furthermore, removal of salts only during the final isolation of sucralose results in a waste stream that contains a high concentration of salts, as well as other impurities. The high level of salts in the waste stream makes the treatment of the waste stream difficult. It would be advantageous if the concentration of salts both in the process stream and also in the waste stream obtained during the final isolation of sucralose could be minimised.

SUMMARY OF THE INVENTION

With the above in mind, the present inventors have devised an improved process for the production of sucralose. In one aspect, the present invention provides a method for producing sucralose from a feed stream resulting from the chlorination of a sucrose-6-acylate in a reaction vehicle. The feed stream includes a sucralose-6-acylate, the reaction vehicle, water, and salts. The salts include one or more selected from the group consisting of alkali metal chlorides, alkaline earth metal chlorides and ammonium chloride. The method includes:

(i) deacylation of the sucralose-6-acylate by treatment with a base to afford a product stream comprising sucralose;

(ii) partial removal of water and, optionally, reaction vehicle from the product stream of (i) in order to cause precipitation of the salts from the product stream;

(iii) removal of the precipitated salts from the product stream of (ii); and (iv) isolation of sucralose from the product stream of (iii).

Various advantageous embodiments and further developments of the process according to the present invention are set out in the dependent claims.

BRIEF DESCRIPTION OF THE DRAWING

FIG. 1 shows a simplified process diagram illustrating a preferred embodiment of the present invention.

DETAILED DESCRIPTION OF THE INVENTION

Thus, according to the present invention, the feed stream from the chlorination of sucrose-6-acylate is subjected to deacylation to afford a product stream comprising sucralose, and then water and, optionally, reaction vehicle are removed from this product stream in order to cause precipitation of the salts. The precipitated salts are then removed from the product stream, and sucralose is isolated from the resulting product stream.

The removal of salts from the process stream of the present invention prior to the isolation of sucralose provides a number of advantages. One advantage is that the waste stream produced during the isolation of sucralose has a much lower salt content than the waste streams of prior art processes, which allows the waste stream to be treated more easily.

A further advantage of the process according to the present invention is that the volume of water that is present in the process stream subsequent to the removal of salts is significantly reduced, which allows significant energy savings to be made downstream. This saving is especially notable if the reaction vehicle is subsequently removed by steam stripping, and could enable the energy costs for steam stripping to be reduced by as much as 75 to 80%.

The reduction in water content that is possible in the process of the present invention was not possible in prior art processes, since sufficient water needed to be present to ensure that the high concentration of salts remained in solution, and to ensure that the sucralose-6-acylate remained in solution when the reaction vehicle was removed. According to the present invention, however, the salts are removed from the process stream, after which the problem of maintaining them in solution is no longer present. Furthermore, the present invention provides that deacylation takes place on the chlorination feed stream, in the presence of reaction vehicle, to provide a process stream containing sucralose, rather than sucralose-6-acylate. By virtue of having a further free hydroxyl group in place of an ester group, sucralose is more soluble in water than sucralose-6-acylate. This higher solubility means that less water needs to be present downstream of the deacylation to maintain the desired species in solution.

In the light of EP 0708110, it is surprising that deacylation can be carried out in an effective manner on the chlorination feed stream in the presence of the reaction vehicle. According to EP 0708110, it was preferred to remove the reaction vehicle prior to carrying out deacylation. This order was preferred in order to avoid decomposition of the reaction vehicle under the deacylation conditions, which reduced the yield of reaction vehicle available to be recovered and subsequently recycled. It also introduced decomposition products as impurities in the product stream.

Contrary to the teaching of EP 0708110, it has now been found that, provided that the reaction conditions are controlled carefully, deacylation can be achieved with minimal decomposition of the reaction vehicle, usually a tertiary amide. Accordingly, it is possible to carry out deacylation prior to the removal of the reaction vehicle, and to then recover the reaction vehicle from a process stream containing sucralose.

Besides allowing for a reduction in the amount of water that needs to be present in the process stream in order to maintain the desired species in solution, the ability to perform deacylation in the presence of the reaction vehicle has a number of further advantages for the process, especially where the reaction vehicle is subsequently removed by steam stripping. These advantages include the fact that the undesired solids that are generated by the steam stripping process are less inclined to trap significant quantities of the desired product. Accordingly, the final yield of sucralose is increased.

A simplified process diagram illustrating a preferred embodiment of the present invention is shown in FIG. 1 for reference.

As used herein, the term "reaction vehicle" means the diluent or solvent in which the chlorination reaction is performed. The term is meant to indicate that the vehicle may not fully dissolve all the components of the reaction and product mixture.

The sucralose-6-acylate can be any acylate that serves to protect the 6-hydroxy group during the chlorination reaction. It is preferably an aliphatic or carbocyclic aromatic acylate, more preferably a benzoate or acetate, and most preferably an acetate.

The chlorination reaction to produce the feed stream that is the starting point for the method of the present invention can be carried out by a number of methods, such as those disclosed in EP 0043649. Depending on the chlorination reagent employed, a number of types of reaction vehicles may be used, and any reaction vehicle can be used that is stable under the chlorination conditions and that dissolves the starting materials, reagents, and products at least to some extent, for example aromatic hydrocarbons such as xylene or toluene; chlorinated hydrocarbons such as trichloroethane; or tertiary amides such as dimethylformamide (DMF).

Preferably, the chlorination is carried out as described in EP 0409549. In that case, a tertiary amide is the reaction vehicle used in the chlorination reaction, and can be any tertiary amide that is stable under the chlorination conditions and that dissolves the starting materials, reagents, and products at least to some extent. The tertiary amide is typically dimethylformamide (DMF).

The nature of the salts present in the chlorination feed stream depends upon the choice of agent for quenching excess chlorination agent. Examples of suitable quenching agents include alkaline earth or alkali metal hydroxides and ammonium hydroxide. Preferred quenching agents are sodium hydroxide and ammonium hydroxide, and sodium hydroxide is particularly preferred. The corresponding chloride salts are formed during the quenching reaction.

The feed stream from the chlorination reaction is treated with a base to effect deacylation of the sucralose-6-acylate and to afford a product stream comprising sucralose. In order to minimise decomposition of the reaction vehicle, the deacylation is preferably carried out under carefully controlled conditions. Therefore, according to the present invention, the deacylation is preferably performed at a pH of from 10 to 13.5, more preferably from 10 to 12, and most preferably from 10.5 to 11.2, at a temperature of from 60 to 0° C., more preferably from 40 to 0° C., and most preferably from 35° C. to 25° C., the higher pH being used with the lower temperature and vice versa.

Suitable bases for use in the deacylation reaction include ammonium hydroxide and metal hydroxides, in particular alkali or alkaline earth metal hydroxides. A particularly preferred base is sodium hydroxide. Other suitable bases known to the skilled person may also be used.

The deacylation reaction can be conveniently monitored by HPLC. For optimum yields, it is important to monitor the progress of the deacylation reaction, and neutralise the reaction mixture when the reaction is complete. The pH of the reaction mixture should be adjusted to from 6 to 8.5, preferably approximately 7.5. The reaction mixture can conveniently be neutralised using dilute hydrochloric acid, or using citric acid or acetic acid. Alternatively, the reaction mixture can be neutralised with gaseous carbon dioxide.

Following deacylation, water and, optionally, reaction vehicle are partially removed from the resulting product stream comprising sucralose. This causes the salts to reach their limiting solubility in the stream, and to precipitate, while the desired sucralose remains in solution in the remaining water and reaction vehicle.

The partial removal of water and, optionally, reaction vehicle can be carried out by any suitable method known to the skilled person, and is preferably carried out by evaporation. Suitable apparatus includes a flash vessel. On a small scale, a rotary evaporator is a suitable choice. Typically, at least 95% of the water present in the mixture at the end of deacylation is removed during this step. More typically, at least 98% is removed.

The precipitated salts can be removed from the product stream by any suitable technique known to the skilled person. Preferably, the removal of the precipitated salts is carried out by filtration. Suitable filtration techniques include rotary vacuum filtration apparatus, a pressure filter apparatus, or a gravity filter apparatus. Non-filtration techniques may also be used, and suitable non-filtration techniques include a centrifuge, a cyclone, or decantation. Typically, at least 50% of the salts present in the mixture at the end of deacylation is removed during this step. More typically, at least 75% is removed. In one preferred embodiment, at least 85% is removed.

Following their removal from the product stream, the precipitated salts are preferably washed with a suitable washing solvent to recover any sucralose that may have been removed with the precipitate, and to thereby maximise the yield of sucralose. The washing liquor is then preferably returned to the sucralose product stream, or alternatively back to an earlier feed stream. Suitable washing solvents can be solvents in which sucralose is soluble but the precipitated salts are not soluble. For example, the washing solvent may be the same as the reaction vehicle.

Alternatively, if the quantity used is carefully controlled, water can be used as the washing solvent without significant quantities of salts being redissolved. This has the advantage that the salts are obtained in a clean form, that is substantially free of reaction vehicle. The salts can then be used directly for another application, without the need for any further processing. Brine solutions, and more particularly saturated brine solutions, may also be used as the washing solvent. This further reduces the quantity of salts that is redissolved, while still resulting in recovered salts that are substantially free of reaction vehicle and can be used directly for another application.

Following the removal of the precipitated salts, the sucralose is isolated from the resulting product stream. Preferably, the reaction vehicle remaining in the sucralose product stream following the removal of precipitated salts is at least partially removed from the product stream, and isolation of sucralose then takes place from the resulting product stream.

The removal of reaction vehicle can be carried out by means known in the art, such as distillation, distillation under reduced pressure, steam distillation, steam stripping, or by use of an agitated thin film drier or spray drier. When the reaction vehicle is a tertiary amide, it is preferred that the removal of the reaction vehicle is carried out by steam stripping. Such steam stripping can be carried out as described in EP 0708110. Typically, at least 90% of the reaction vehicle present in the mixture at the end of deacylation is removed during this step. More typically, at least 99% is removed.

When carried out in the context of the present invention, steam stripping to remove reaction vehicle requires substantially less energy than in prior art processes, since far less water is present in the product stream. Energy costs for the steam stripping can thus be reduced by as much as 75-80%. The environmental impact of the process is thus significantly reduced.

In addition to the advantages already mentioned, the removal of salts from the sucralose product stream also opens up the possibility of employing salt-sensitive processing steps on the downstream product stream. The presence of high concentrations of salts in prior art sucralose product streams prevented such processing steps from being able to be used.

The present inventors have recognised a particularly beneficial opportunity to take advantage of the low salt product stream provided according to the present invention. In particular, they have recognised that the low salt product stream can be subjected to an improved process for the removal of dimethylamine (DMA).

DMA is the hydrolysis product of DMF. When DMF is used as reaction vehicle in the chlorination of sucrose-6-acylate and in the subsequent deacylation of sucralose-6-acylate, the reaction conditions, and in particular the elevated pH during the deacylation step, result in some DMF hydrolysis and consequent formation of DMA. Typically, around 4-20 moles of DMF are converted to DMA per mole of sucralose.

DMF hydrolysis to produce DMA is undesired for a number of reasons. A first reason is that the DMF that is converted to DMA cannot be directly recycled for re-use in the sucralose production process. This loss of valuable DMF imposes a significant financial burden on the process. A further reason is that the presence of DMA in product and waste streams causes difficulties in downstream processing steps.

One possible strategy for removing DMA from a sucralose product stream is to increase the pH in order to free the DMA from its counter-ion containing salts, and to then remove the relatively volatile free DMA by applying heat and reduced pressure. However, these conditions can result in degradation of sucralose and other valuable carbohydrates in the stream, and are also expensive to apply. Accordingly, it would be advantageous to be able to remove DMA under more gentle conditions, so as to maintain the yield of sucralose and other valuable carbohydrates.

It has now been found that DMA can be effectively removed from a low salt product stream, such as that provided according to the present invention, by making use of a cation exchange resin. This technique cannot be used on sucralose product streams according to the prior art, since the high concentration of salts in such streams renders the cation exchange resin ineffective. This is because the cations from the salts present in the streams (such as $Na^+$ ions from NaCl) occupy the binding sites of the cation exchange resin, so that few or no binding sites are available to bind DMA (in the form of its cation, $DMAH^+$, which has a $pK_a$ of 10.73). In the case of low salt product streams, however, this problem is significantly reduced, so that effective binding of $DMAH^+$ to the cation exchange resin is possible.

Thus, according to a further aspect of the present invention, there is provided a process according to the first aspect of the present invention, wherein the process further comprises contacting the product stream with an ion exchange resin after the removal of the precipitated salts. Preferably, the contacting of the product stream with the ion exchange resin takes place by passing the stream through a column loaded with the ion exchange resin or through a bed comprising the ion exchange resin.

Suitable cation exchange resins for use with the present invention are those that can bind $DMAH^+$ while allowing sucralose and other valuable carbohydrates to pass through substantially unchanged. Strong acid cation exchange resins, such as those containing a sulfonate group or other acidic group, have shown themselves to be particularly suitable, and are preferred. Particularly preferred examples of suitable cation exchange resins are Purolite® C120E (available from Purolite) and Dowex® HCRS (available from Dow). Other cation exchange resins that would be suitable for use in the present invention include Purolite® C100E (available from Purolite), Finex® CS 08 G (available from Finex), Finex® CS12 G (available from Finex), Finex® 18 G (available from Finex), Purolite® C100 series (available from Purolite), Purolite® C150 series (available from Purolite), Purolite® PCR series (available from Purolite), Amberlite® IR120 series (available from Rohm & Haas), and DIAION® SK, PK, and UBK series (all available from Mitsubishi Chemical). Yet further cation exchange resins that may be contemplated for use in the present invention include Dowex® 88 (available from Dow) and Purolite® 104E (available from Purolite).

According to a preferred embodiment, the removal of DMA from a sucralose product stream of the present invention takes place after the removal of precipitated salts and after remaining reaction vehicle (DMF) has been at least partially removed from the desalinated product stream, which will preferably have taken place by steam stripping. The product stream will therefore be essentially aqueous. If necessary, further water can be added to dilute the product stream and to adjust the viscosity as required.

In order to protect the cation exchange resin, it is preferable to subject the product stream to a filtration step prior to contacting it with the cation exchange resin. Any suitable filtration procedure known to the skilled person can be used for this purpose.

The cation exchange resins for use in the present invention can be prepared according to techniques known in the art. A preferable method for preparing the cation exchange resins for use is to treat them either with a sodium chloride solution or with a sodium hydroxide solution. These solutions are known as "regenerants". In the case of a sodium chloride solution, the preferred solution concentration is from 5 to 20%, and is most preferably about 10%. In the case of a sodium hydroxide solution, the preferred solution concentration is from 2 to 20%, and is most preferably around 5%. Following the treatment with regenerant, the resins are rinsed with deionised water. In the case where a sodium chloride solution is used as regenerant, rinsing is preferably continued until the sodium chloride content of the rinse water reaches about 400 ppm or lower. In the case where a sodium hydroxide solution is used as regenerant, rinsing is preferably continued until the pH of the rinse water reaches about pH 10 or lower.

Following preparation of the cation exchange resin, for example as set out above, it can be packed to form a resin bed/loaded to form a resin column. The quantity of resin used for a particular volume of feed stream can be selected by performing preliminary calculations and optimisation experiments for the particular resin and feed stream used.

The total ion exchange capacity of an ion exchange resin is the theoretical maximum quantity of ions that can be bound by a particular resin, and will generally be advertised by the manufacturer. In general, this parameter is quoted in units of "equivalents per liter of resin". If a particular resin has a total ion exchange capacity of 1 equivalent per liter, then it is theoretically capable of binding a maximum of one mole of singly-charged ions per liter of resin.

While the total ion exchange capacity of a particular ion exchange resin will generally be known, it should be noted that the operating capacity of the resin in a particular system will often be less than the total ion exchange capacity. The operating capacity can be calculated by routine experimentation for any particular system.

In addition to the operating capacity of the resin being used, additional parameters that can usefully be calculated are the number of equivalents of the ion to be removed per liter of feed stream (in the present case, this will be the number of moles of $DMAH^+$ per liter of feed stream) and the volume of feed stream to be treated.

With the above parameters to hand, it is possible to calculate the amount of feed (in liters) that can be treated by a given volume of resin as follows:

$$\frac{\text{Volume of Resin(L)} \times \text{Operating Capacity of Resin(Equivalents per Liter)}}{[\text{Equivalents of } DMAH^+ (\text{moles per Liter of feed})/\text{Volume of Feed(L)}]}$$

The above information, together with routine experimentation, will allow the skilled person to optimise the system for particular resins and feed concentrations.

Following preparation of the resin bed/column, the product stream can then be passed through the resin to at least partially remove DMA. The more salts that can be removed from the sucralose product stream prior to its being contacted with a cation exchange resin, the more effective the binding of $DMAH^+$ to the resin will be, and the more DMA will therefore be removed. Accordingly, in this aspect of the present invention, it is preferred to remove as much salt as practicable from the product stream prior to its being contacted with a cation exchange resin, while keeping cost and the overall efficiency of the process in mind. Thus, it is preferred to remove at least 50% of the salts, more preferably at least 75% of the salts, and most preferably at least 85% of the salts prior to the contacting of the product stream with the cation exchange resin.

As has been discussed previously, it is desirable to wash the precipitated salts following their removal from the product stream, in order to recover any sucralose or other valuable carbohydrates that may have been removed with the precipitated salts. The washing liquor can then be added back into the product stream in order to maintain yields. In the case where it is intended to contact the product stream with an ion exchange resin, it may often be preferable to combine the washing liquor from the washing of the precipitated salts with the product stream downstream of the product stream being contacted with the ion exchange resin. The reason for this is that, while this washing liquor may contain valuable carbohydrates, it may also include some re-dissolved salts.

The conditions for achieving optimum performance of the cation exchange resins used in the present invention may vary according to the resin used and can be determined by routine experimentation. As a guide, optimum performance of the cation exchange resins might be expected when the pH of the product stream is in the range of from about 7 to about 9, and preferably around 7, and when the temperature of the product stream is in the range of from about 10 to about 50° C., and preferably around room temperature.

The amount of DMA that can be removed from the product stream according to this aspect of the present invention will vary according to the factors already mentioned, such as the concentration of residual salts, temperature and pH of the product stream and so on. However, in general, it is preferred that at least 70% of the DMA present prior to contacting the stream with cation exchange resin is removed, more preferably at least 95%, and most preferably at least 99%.

After use, i.e. after the resin's capacity to bind further $DMAH^+$ is no longer sufficient, the resin bed/column is preferably flushed with deionised water to remove any sucralose and other valuable carbohydrates, and the flush liquor can then be combined with the remaining product stream to maintain yields.

Removal of bound $DMAH^+$ from the cation exchange resin is preferably carried out in the same manner as the initial preparation of the resin detailed above, i.e. by treating with a regenerant and then rinsing with deionised water. Following this, the resin is ready to be reused.

In a particularly preferred embodiment, the recovered DMA is subjected to conditions effective to convert it back into DMF. An example of appropriate conditions for effecting this conversion is the use of carbon monoxide and catalytic amounts of sodium methoxide. This conversion is known in the art, and so no further details need be given here. The regenerated DMF can then be reused as the reaction vehicle in the production of sucralose. This recovery of DMF that would have been lost in prior art processes provides a significant economic as well as an environmental advantage.

Eventual isolation of sucralose in the method of the present invention, regardless of whether or not DMA has been removed from the product stream, will usually be carried out as described in EP 0708110.

The invention will now be illustrated by means of the following examples, it being understood that these are intended to explain the invention, and in no way to limit its scope.

EXAMPLES

Example 1

General

The feed stream came from the chlorination of sucrose-6-acetate with phosgene/dimethylformamide, after quenching with sodium hydroxide solution. Such a feed stream can be produced, for example, by the methods disclosed in EP 0 409 549. A typical composition of the feed stream from the chlorination reaction is as follows:

| Description | % of total |
| --- | --- |
| Water | 49% |
| Dimethylformamide | 32% |
| Sodium chloride | 8% |
| Dimethylammonium hydrochloride | 4% |
| Sucralose-6-acetate | 3% |
| Sodium acetate | 1% |
| Others | 3% |

Deacetylation:

A sample of deacetylated product was synthesised as described below.

527 g of the above chlorination feed stream was continuously adjusted to pH 10.5 at 40° C. over a period of 4 hrs by dropwise addition of a total of 59 g of 27% NaOH solution. The progress of the deacetylation reaction was monitored using HPLC. When the deacetylation reaction was complete, the pH of the reaction mixture was lowered to pH 7 by adding 24.5 g of 20% HCl solution, over a period of 15 minutes.

Analysis of the deacetylated material showed it had the following composition:

| Deacetylation Feed | |
| --- | --- |
| | % as is |
| Water | 49% |
| DMF | 32% |
| Sucralose | 2% |
| NaCl | 8% |
| Others | 9% |

Removal of Salts:

About 102 g of the deacetylated material was placed in the round bottom flask of a rotary evaporator and was rotary evaporated under vacuum at 75° C. in order to remove water and DMF from the system. Due to the different boiling points of water and DMF (100° C. and 155° C.) proportionately more water is removed than DMF in this simple one step concentration/evaporation lab process. The composition of the mixture after concentration is shown below:

| | Deac Feed | | Concentrator | |
| --- | --- | --- | --- | --- |
| Weight/g | 101.6 | | 43.4 | |
| Dissolved Solids/% | 19% | | 44% | |
| Dissolved Solids/kg | 19.3 | | 19.3 | |
| | % as is | g | % as is | g |
| Water | 49% | 50.3 | 0% | 0.1 |
| DMF | 32% | 32.0 | 55% | 24.0 |
| Sucralose | 2% | 2.1 | 5% | 2.1 |
| NaCl | 8% | 7.7 | 18% | 7.7 |
| Others | 9% | 9.5 | 22% | 9.5 |

On evaporation of the mixed solvents, a precipitate was formed. This precipitate could be readily separated from the mother liquor by filtration under vacuum on a Buchner funnel. The analysis of the filter cake (predominantly salt—NaCl) and the filtrate is shown below:

| | Salt | | Filtrate | |
| --- | --- | --- | --- | --- |
| Weight/g | 13.1 | | 30.3 | |
| Dissolved Solids/% | 95% | | 23% | |
| Dissolved Solids/kg | 12.5 | | 6.9 | |
| | % as is | g | % as is | g |
| Water | 0.03% | 0.0 | 0% | 0.1 |
| DMF | 5% | 0.7 | 77% | 23.4 |
| Sucralose | 1% | 0.1 | 7% | 2.0 |
| NaCl | 56% | 7.3 | 1% | 0.4 |
| Others | 38% | 5.0 | 15% | 4.5 |

The filter cake is dark brown in colour and contains residual sucralose and DMF, as well as other impurities, "others" (colour bodies etc). It is desirable to recover both the sucralose and the DMF components, so the salt cake was washed with a roughly equal volume of water (12.7 g) at room temperature. Analysis of the washed salt and the salt wash are shown below.

|                     | Washed salt |      | Salt Wash |      |
|---------------------|-------------|------|-----------|------|
| Weight/g            | 10.0        |      | 12.9      |      |
| Dissolved Solids/%  | 96%         |      | 22%       |      |
| Dissolved Solids/kg | 9.6         |      | 2.9       |      |
|                     | % as is     | g    | % as is   | g    |
| Water               | 4%          | 0.4  | 73%       | 9.4  |
| DMF                 | 0.3%        | 0.03 | 5%        | 0.6  |
| Sucralose           | 0.1%        | 0.01 | 1%        | 0.1  |
| NaCl                | 58%         | 5.8  | 12%       | 1.5  |
| Others              | 38%         | 3.8  | 10%       | 1.3  |

This analysis shows that washing of the salt results in good removal of DMF and sucralose into the wash water phase. It also shows, as expected, that some of the NaCl is dissolved into the wash water. The amount of salt that dissolves in the wash water is a function of the mass of water used (relative to the mass of cake) as well as the temperature of the water.

In order to recover as much of the sucralose (and DMF) as possible, the wash water and filtrate were combined. This mixture was then stripped in the laboratory (on the rotary evaporator by successive additions of water and evaporations) to give the final stripped product as shown below:

|                     | Combined Filtrate & Salt Wash |      | Stripped product |      |
|---------------------|-------------------------------|------|------------------|------|
| Weight/g            | 43.2                          |      | 25.7             |      |
| Dissolved Solids/%  | 23%                           |      | 38%              |      |
| Dissolved Solids/kg | 9.7                           |      | 9.7              |      |
|                     | % as is                       | g    | % as is          | g    |
| Water               | 22%                           | 9.5  | 62%              | 16.0 |
| DMF                 | 56%                           | 24.0 | 0%               | 0.0  |
| Sucralose           | 5%                            | 2.1  | 8%               | 2.1  |
| NaCl                | 4%                            | 1.9  | 7%               | 1.9  |
| Others              | 13%                           | 5.7  | 22%              | 5.7  |

This procedure gives a means of removing much of the salt from the process whilst maintaining a high recovery of the DMF and the sucralose (99.5% recovery of sucralose).

Example 2

In order to demonstrate the removal of DMA from a low salt sucralose product stream using cation exchange resins, the following procedures were carried out:
Preparation of the Resin Bed:
A resin bed was prepared by washing a strong cation exchange resin, such as Dowex® HCRS or Purolite® C120E, with either 10% NaCl or 5% NaOH. The washed resin was then packed with deionised water to form a resin bed, and then flushed with deionised water to flush the resin bed of regenerate.
Preparation of a Suitable Test Stream:
A test stream was prepared by following the procedures described in EP0708110 to obtain deacetylated steam strip bottoms.
Removal of Salts:
Salts were removed from the test stream by evaporating water to cause precipitation of the salts and subsequent filtration to remove the precipitated salts. If necessary, the filtrates were diluted with water to adjust the viscosity. The filtrates were then used in the Examples below:

Example 2a (Comparative)

A filtrate containing 5.4 wt % sucralose, 8 wt % chloride, 35,000 ppm sodium ions and 23,000 ppm DMA was charged to the prepared resin bed (Dowex® HCRS) such the total amount of DMA applied was 35.8 g. The bed was then rinsed with deionised water and the effluent was analysed for its DMA content. It was found that 4 g of DMA had bound to the resin. A resin capacity of 0.32 equivalents per liter of resin was thereby calculated.

Example 2b

A filtrate stream containing 15 wt % DMA and 2.3 wt % sodium was diluted with water to adjust its viscosity. This stream was charged to a bed of Dowex® HCRS resin prepared as above, in an amount of 3 equivalents of DMA per liter of packed resin. The bed was then rinsed with deionised water and the effluent was analysed for its DMA content. It was found that 78% of charged DMA had bound to the resin.

Example 2c

The Example 2b was repeated but 2 equivalents of DMA per liter of packed resin was charged to the resin bed. It was found that 92% of charged DMA was retained on the resin.

Example 2d

The Example 2b was repeated but 1 equivalent of DMA per liter of packed resin was charged to the resin bed. It was found that 100% of charged DMA was retained on the resin.

Example 3

In order to further demonstrate the removal of DMA from a low salt sucralose product stream using cation exchange resins, the following procedures were carried out:
Preparation of a Suitable Test Stream:
Sucralose-6-acetate was subjected to chlorination according to the procedures described in EP0708110 to provide a chlorination mass.
1646 g of the chlorination mass (36.5% DMF, 2.4% sucralose-6-acetate, 29000 ppm DMA, 7.4% chloride) was deacetylated for 6 hours at pH 12.4, 11.4° C. by addition of 10% NaOH. Concentrated HCl was used to reduce the pH to 8.3. 2090 g product was collected containing 2.2% sucralose, 6.9% (142 g) chloride, and 15600 ppm DMA (32 g DMA total). 2067 g of this material was concentrated to 686 g which was filtered producing a 229 g wet salt cake and 461 g concentrated filtrate. The concentrated filtrate contained 60700 ppm DMA (28 g) and 56% DMF (258 g).
Removal of Salts:
The concentrated filtrate obtained above was diluted 1:4 with water to adjust its viscosity and was then run through a column packed with 1.3 L Mitsubishi UBK 510L resin (prepared by washing with 5% NaOH and rinsing with deionised water). The column was washed with deionised water to displace carbohydrate and 2227.3 g effluent was collected. This contained 11.5% (257 g) DMF, 0.2% chloride (4.5 g) and 321 ppm DMA (0.72 g). The DMA removal in this case was 97.4%.

The invention claimed is:
1. A method for producing sucralose from a feed stream resulting from the chlorination of a sucrose-6-acylate in a reaction vehicle, said feed stream comprising a sucralose-6-acylate, the reaction vehicle, water, and salts, said salts including one or more selected from the group consisting of alkali metal chlorides, alkaline earth metal chlorides and ammonium chloride, wherein said method comprises:

(i) deacylation of the sucralose-6-acylate by treatment with a base to afford a product stream comprising sucralose;
(ii) partial removal of water and, optionally, reaction vehicle from the product stream of (i) to produce a product stream including a liquid phase and precipitated salts;
(iii) removal of the precipitated salts from the product stream of (ii); and
(iv) isolation of sucralose from the product stream of (iii).

2. The method according to claim 1, wherein the remaining reaction vehicle is at least partially removed from the product stream of (iii), and isolation of sucralose takes place from the resulting product stream.

3. The method according to claim 2, wherein the removal of reaction vehicle from the product stream of (iii) is performed by steam stripping, or by use of an agitated thin film drier or spray drier.

4. The method according to claim 1, wherein the removal of water and, optionally, reaction vehicle from the product stream of (i) is performed by evaporation.

5. The method according to claim 4, wherein the removal of water and, optionally, reaction vehicle from the product stream of (i) is performed in a flash vessel.

6. The method according to claim 1, wherein the precipitated salts are removed by filtration.

7. The method according to claim 6, wherein the filtration is performed using a rotary vacuum filtration apparatus, a pressure filter apparatus, or a gravity filter apparatus.

8. The method according to claim 1, wherein the precipitated salts are removed by a non-filtration technique.

9. The method according to claim 8, wherein the precipitated salts are removed by a centrifuge, a cyclone, or by decantation.

10. The method according to claim 1, wherein the precipitated salts are washed with a washing solvent, and the resulting washing liquor is combined with the product stream of (iii).

11. The method according to claim 10, wherein the washing solvent is the same as the reaction vehicle.

12. The method according to claim 10, wherein the washing solvent is water.

13. The method according to claim 10, wherein the washing solvent is a brine solution.

14. The method according to claim 13, wherein the brine solution is saturated.

15. The method according to claim 1, wherein the sucralose-6-acylate is sucralose-6-benzoate or sucralose-6-acetate.

16. The method according to claim 15, wherein the sucralose-6-acylate is sucralose-6-acetate.

17. The method according to claim 1, wherein the salts consist essentially of sodium chloride.

18. The method according to claim 1, wherein the base used in the deacylation is ammonium hydroxide or a metal hydroxide.

19. The method according to claim 18, wherein said base is an alkali or alkaline earth metal hydroxide.

20. The method according to claim 19, wherein said base is an alkali metal hydroxide.

21. The method according to claim 20, wherein said base is sodium hydroxide.

22. The method according to claim 1, wherein said deacylation is carried out at a pH of from 8 to 14 and a temperature of from 0 to 60° C.

23. The method according to claim 22, wherein said deacylation is carried out at a pH of from 10 to 12 and a temperature of from 0 to 40° C.

24. The method according to claim 1, wherein the reaction vehicle is a tertiary amide.

25. The method according to claim 24, wherein the tertiary amide is dimethyl formamide (DMF).

26. The method according to claim 1, wherein the method further comprises contacting the product stream with an ion exchange resin after the removal of precipitated salts.

27. The method according to claim 26, wherein the ion exchange resin is a cation exchange resin.

28. The method according to claim 27, wherein a strong cation exchange resin is used as the cation exchange resin, and wherein the strong cation exchange resin contains a sulfonate group or other acidic group.

29. The method according to claim 28, wherein Purolite® C120E or Dowex® HCRS is used as the cation exchange resin.

30. The method according to claim 26, wherein the contacting of the product stream with the ion exchange resin takes place after remaining reaction vehicle has at least partially been removed from the product stream.

31. The method according to claim 26, wherein the product stream is essentially aqueous when contacted with the ion exchange resin.

32. The method according to claim 26, wherein the product stream is filtered prior to being contacted with the ion exchange resin.

33. The method according to claim 26, wherein the ion exchange resin is flushed with a flushing solvent after it has been contacted with the product stream, and wherein the flushing liquor thereby obtained is combined with the downstream product stream.

34. The method according to claim 33, wherein the flushing solvent is deionised water.

35. The method according to claim 26, wherein the ion exchange resin is treated with a regenerant after it has been contacted with the product stream.

36. The method according to claim 35, wherein the regenerant is selected from the group consisting of an aqueous sodium chloride solution or an aqueous sodium hydroxide solution.

37. The method according to claim 35, wherein the regenerant is subsequently collected.

38. The method according to claim 37, wherein the collected regenerant comprises dimethyl amine (DMA).

39. The method according to claim 38, wherein the DMA is subjected to reaction conditions effective to convert DMA into DMF.

40. The method according to claim 35, wherein the ion exchange resin is re-used after having been treated with the regenerant.

41. The method according to claim 26, wherein the precipitated salts are washed with a washing solvent, and the resulting washing liquor is combined with the product stream downstream of its being contacted with an ion exchange resin.

* * * * *